(12) United States Patent
Ripperger

(10) Patent No.: US 7,153,962 B1
(45) Date of Patent: Dec. 26, 2006

(54) PROCESS FOR GENTLY COOLING AND CRYSTALLIZING MELAMINE FROM A MELAMINE MELT OR FROM THE GASEOUS PHASE

(75) Inventor: Willi Ripperger, Frankenthal (DE)

(73) Assignee: Casale Chemicals S.A. (CH)

( * ) Notice: Subject to any disclaimer, the term of this patent is extended or adjusted under 35 U.S.C. 154(b) by 0 days.

(21) Appl. No.: 11/179,368

(22) Filed: Jul. 12, 2005

(51) Int. Cl.
*C07D 251/62* (2006.01)
*C07D 251/60* (2006.01)

(52) U.S. Cl. ...................................... 544/203; 544/201
(58) Field of Classification Search ................ 544/203, 544/201
See application file for complete search history.

(56) References Cited

U.S. PATENT DOCUMENTS

| 2,755,887 A | * | 7/1956 | Boatright et al. | ........... 544/203 |
| 5,514,796 A | | 5/1996 | Best et al. | |

FOREIGN PATENT DOCUMENTS

| EP | 1 035 117 A1 | 9/2000 |
| EP | 1 248 254 A3 | 10/2004 |

OTHER PUBLICATIONS

Ullmann's Encyclopedia of Industrial Chemistry, vol. A 16, 5th Edition pp. 171-185 (1990).

\* cited by examiner

*Primary Examiner*—Venkataraman Balasubramanian
(74) *Attorney, Agent, or Firm*—Akerman Senterfitt

(57) ABSTRACT

Process for cooling and crystallizing solid melamine from the gaseous phase or from melamine melts as they develop in technical processes used to produce melamine, characterized in that the melamine-containing process gases or melamine melts are introduced into liquid, organic phase at high pressure, said phase comprising polyvalent alcohols such as ethylene glycol, glycerine or their homologous series or of amines such as ethanol amines or a mixture of both groups. The advantage this process is that the hot melamine is cooled very quickly without forming thermal decomposition products and that during quenching no reaction of the melamine with the solvent occurs, the formation of higher deammoniation products such as melam and melem is prevented and higher deammoniation products of the melamine such as melam and melem, are partially converted back into melamine.

7 Claims, 1 Drawing Sheet

PROCESS FOR GENTLY COOLING AND CRYSTALLIZING MELAMINE FROM A MELAMINE MELT OR FROM THE GASEOUS PHASE

FIELD OF APPLICATION

In its more general aspect, the present invention relates to a process for gently cooling and crystallizing melamine from melamine melt or from the gaseous phase.

In particular, the present invention concerns a process for the continuous cooling and crystallization of solid melamine from the gaseous phase or from melamine melts as they develop in technical processes used to produce melamine.

PRIOR ART

Melamine is technically produced using two processes through the decomposition of urea at about 400° C. and in the presence of ammonia: either by converting urea in the presence of a catalyst at low pressure (up to 2 MPa) or at high pressure (7–15 MPa) in a purely thermal reaction. The various processes are described in "Ullmann's Encyclopedia of Industrial Chemistry, Vol. A 16, 5$^{th}$ Edition, pages 171–185 (1990)".

In the catalytic low-pressure processes the melamine leaves the reactor in a gaseous state, the reaction gas contains apart from melamine also ammonia, carbon dioxide and decomposition products of the urea that has not been converted into melamine. In the BASF process the melamine—after prior separation from catalyst dust and melem—is desublimated into fine-grained melamine through the addition of cold reaction gas from the gaseous phase. The disadvantage with this process is that too high a cooling gas quantity is required in order to precipitate the melamine from the gaseous phase and that a very fine-grained melamine is obtained. Since in this process after the melamine desublimation no further cleaning step follows, high demands are placed on conducting the reaction in order to prevent the formation of by-products.

In the catalytic processes by Chemie Linz and DSM, the melamine is precipitated from the gaseous phase by means of quenching with an aqueous melamine suspension. The disadvantage of a water quenching step is that during quenching a portion of the melamine is hydrolyzed into oxotriazines, thus necessitating recrystallization of the melamine as well as a complex waste water treatment. Another disadvantage consists in the fact that after separation of the melamine a water vapor-containing $NH_3/CO_2$ gas develops, which cannot be subjected to a urea rinsing process.

With the non-catalytic high-pressure processes melamine develops in the reactor as a melamine melt at about 400° C. and pressure of 7 to 15 MPa. Depending on the process conditions, the melt contains still more or less high portions of ammonia and carbon dioxide as well as contaminations of the melamine formed in by-reactions, e.g. ureidomelamine, melam, melem etc. The problem is that at 400° C. melamine is only stable if high ammonia pressure exists. To cool and obtain the melamine, the melamine melt coming from the reactor however must be decompressed and brought to lower pressures and be cooled to temperatures below 350° C., preferably to 200 to 300° C. Quick cooling to prevent $NH_3$ separating from the melamine can technically only be conducted with significant effort. If this cooling process does not take place quickly enough, the separation of ammonia leads to the development of higher molecular condensation products such as melam and melem, which interfere with the subsequent processing of the melamine. Effective quenching is therefore the prerequisite for obtaining melamine in a sufficient purity (>99.8%).

Technically, the cooling process of the melamine melt and conversion of the by-products such as melam or ureidomelamine can take place based on two process options:

a) by quenching with an aqueous, alkalized melamine suspension or solution (Nissan process, U.S. Pat. No. 3,637,686, DE 10229100A, WO 0029393), or b) by quenching with liquid ammonia (U.S. Pat. No. 5,514,796, US 02007061, WO 00/55142).

Quenching with an aqueous, alkalized melamine suspension or solution automatically leads to a stronger hydrolysis of the melamine into oxotriazines and hence to a loss in yield of 2–6% (DE 100 30 453 A1). Due to the formation of hydrolysis products, a portion of the mother liquor must be continuously removed and subjected to further treatment, creating a waste water problem.

The processes for "dry" precipitation with liquid or cold ammonia have not taken hold in practice so far. The reasons for this are manifold: for one, the heat transfer between the cold gas and hot melamine melt is not optimal enough to prevent the formation of deammonation products during the decompression step. Secondly, the amounts of gas created during cooling of the melamine melt and requiring treatment represents an economic disadvantage. Moreover the melamine precipitated by an ammonia quench is very fine-grained; its meal-like consistency makes further handling more difficult. The disadvantages of the "dry" precipitation processes are described in detail for example in EP 1035117.

SUMMARY OF THE INVENTION

The technical problem underlying the present invention is that of providing a process for the continuous and gentle cooling and crystallization of the melamine from a melamine melt or from the gaseous phase without thermal decomposition or hydrolysis of the melamine during the cooling and crystallization operations, so has to overcome the above disadvantages mentioned with reference to the prior art.

Said problem is solved according to the invention by a process of the above-identified type, which is characterized in that a melamine melt, as it develops in technical, non-catalytic high-pressure processes used for melamine production, or a hot reaction gas from a catalytic process containing the gaseous melamine in addition to ammonia, carbon dioxide and unreacted urea, is decompressed or introduced directly into a liquid, organic phase. Polyvalent alcohols such as ethylene glycol, propylene glycol, glycerin and/or other higher alcohols and/or mixtures of said alcohols as well as ethanol amines having the general formula $R_nN(C_2H_5OH)_{3-n}$, wherein R represents an aliphatic radical or an H atom, are suited as the liquid, organic phase. Ethanol amines such as mono-, di- and triethanol amine, methyl diethanol amine and/or their mixtures are especially suitable. The liquid, organic phase can also consist of mixtures of the two afore-mentioned groups of compounds.

The temperature of the liquid, organic phase is maintained during the cooling and crystallization steps, i.e. during the so-called quenching, preferably between 20° C. and 350° C., the pressure can be atmospheric pressure or be slightly below the pressure used for the respective production process. Furthermore the quantity of the liquid, organic phase required for quenching can be selected such that the entire melamine dissolves in the liquid phase or forms a suspension of the melamine and liquid phase. In the first case, in a subsequent process step the melamine is crystallized out of the liquid phase, e.g. by means of cooling, and separated, in the latter case the melamine can be separated from the liquid phase without cooling directly by means of hydrocyclones and/or centrifuges. The process is furthermore characterized in that, after the melamine separation step, the liquid phase is returned to the quenching step. Due to the good water solubility of the afore-mentioned liquid, organic phases, the melamine can be freed from all residue by washing it with water after separation in the centrifuges.

It was surprisingly found that by means of quenching gaseous melamine or a melamine melt with the above-mentioned organic compounds and/or their mixtures, such quick cooling of the gaseous melamine or of the melamine melt occurs that no deammonation products are formed. Surprisingly even at high quenching temperatures no hydrolysis products developed from the reaction with the OH-groups of the alcohols as occurs when quenching with water. Surprising was also the high solubility of the melamine in the listed liquid, organic phases, which represents a great procedural advantage over a suspension process.

Further characteristics and the advantages of the invention shall become clearer from the following description of an embodiment thereof, made for indicating and not limiting purposes, with reference to the attached FIGURE.

DETAILED DESCRIPTION OF A PREFERRED EMBODIMENT OF THE INVENTION

Figure 1:
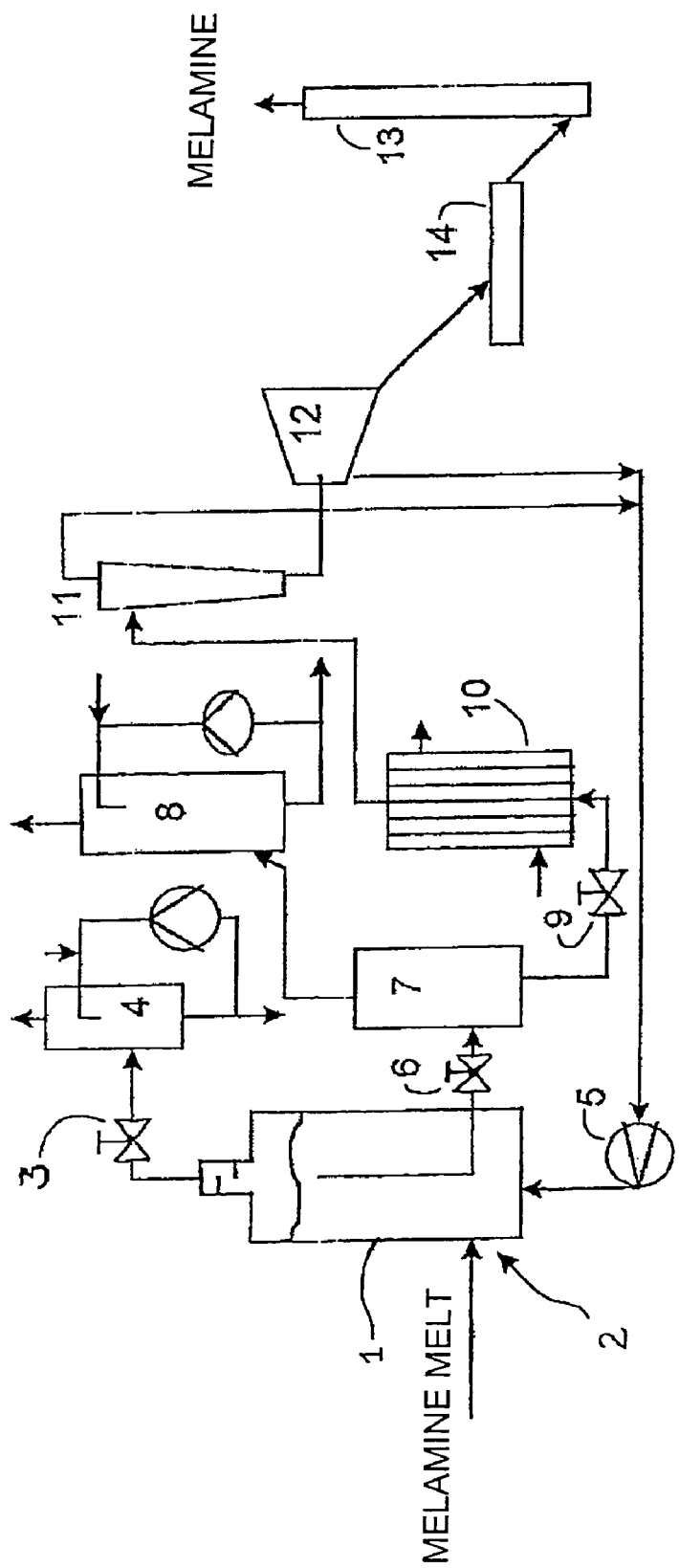
FIG. 1 shows a block diagram illustrating the melamine cooling and crystallization process from a melamine melt or from the gaseous phase, according to the present invention.

In the following, the process according to the present invention using the example of a melamine melt obtained with a non-catalytic high-pressure process is described in more detail with reference to FIG. 1.

In the process according to the invention any melamine melt coming from a technical high-pressure process can be used. The same applies accordingly for gaseous melamine from a catalytic process. The reaction conditions referred to in the description of the process do not represent a restriction; they only serve the explanation and understanding of the process. Those skilled in the art will know that the respective operating conditions have to be adjusted to the physical and chemical properties of the employed liquid, organic phase.

Feeding the melamine melt coming from the melamine synthesis reactor and which has been largely freed from $CO_2$ and excess $NH_3$, into the quencher 1. This step preferably occurs by means of spraying the melamine melt into the prepared liquid, organic phase present in quencher 1 by means of one or more nozzles (of conventional type and thus not shown in FIG. 1) in order to achieve the quickest possible cooling. Preferably, the melamine melt is fed through the spraying nozzles in the lower portion 2 of the quencher 1. It is, however, likewise possible to finely disperse the melamine melt on top of the quencher by means of a nozzle (simple or dual nozzle) and add the liquid, organic phase with additional atomizing cone nozzles. It is important that the contact between the melamine melt and liquid, organic phase occurs quickly and intensively.

The temperature in the quencher 1 is maintained between 20° C. and 350° C., temperatures between 100° C. and 250° C. being particularly advantageous, on one hand in order to ensure sufficient solubility of the melamine in the organic phase, on the other hand in order to prevent decomposition reactions of the liquid phase. Optimal are temperatures that—depending on the pressure conditions in the quencher 1 and stripper 7—are below the boiling point of the employed liquid, organic phase.

The pressure in the quencher depends on the pressure used for the process. High-pressure plants generally operate at a reactor pressure of 7 to 17 MPa, a pressure difference of 0.1–0.5 MPa between the melamine reactor and the quencher is enough to achieve sufficiently fine dispersion of the melamine in the quencher. With the catalytic low-pressure processes the pressure in the quencher needs to be selected correspondingly lower; in this case additionally the feed of the reaction gases and the liquid phase through nozzles on top of the quencher, as described above, is preferable.

Depending on the selected pressure and temperature conditions in the quencher and the amount of gases still contained in the melamine melt ($NH_3$, $CO_2$, HNCO), a portion of these components degases, collects in the upper section of the quencher 1 equipped with liquid separators and is decompressed by means of the pressure retention valve 3 in the washing column 4 and further treated, e.g. by washing it with water.

The circulating quantity of the liquid, organic phase added in the quencher via the pump 5 in the present example is either selected such that the solution leaving the quencher contains 5–8% by weight melamine at an outlet temperature of 100° C. or at higher quench temperatures accordingly more (up to 40% by weight).

Alternatively the temperature and recycle ratio can be adjusted such that a melamine suspension develops, from which the suspended melamine is separated together with the crystallized melamine by means of hydrocyclones and/or centrifuges after cooling. The residence time of the melamine solution or the melamine suspension in the quencher can be adjusted such that deammonation products of the melamine such as melam and melem are converted back into melamine. Since compared to a water quench higher temperatures can be employed in the process according to the invention, these components are converted back to melamine considerably more quickly. As a function of the melam and melem contents of the melamine melt, residence times of 10–60 minutes, preferably 10 to 30 minutes, are sufficient.

From the quencher 1 the melamine-containing solution or suspension is decompressed by means of a relief valve 6 into the $NH_3$ stripper 7. At a pressure of 0.1–2 MPa in the stripper, the remaining dissolved gases are driven out of the solution or suspension and further treated in the washing column 8.

The clear solution or suspension drawn from the bottom of the $NH_3$ stripper by means of the valve 9 is cooled in the cooling unit 10, wherein melamine is largely crystallized out. In the hydrocyclone 11 the majority of the precipitated melamine crystals is separated and washed in the centrifuge 12 with a condensate free of residue. In the dryer 13 the melamine is dried. The residue of the liquid, organic phase contained in the washing water of the centrifuge is recovered in a separate column (not shown) and recycled to the quencher 1 via the pump 5.

So as to keep the portion of organic phase low in the washing water, the melamine can initially be separated by centrifuges without a washing step and be freed from the adhering residue of the organic phase in a subsequent separate apparatus, e.g. band filter 14, by means of washing.

The overflow from the hydrocyclone 11, which still contains fine-grained melamine crystals, is returned into the quencher 1 via the pump 5. By using hydrocyclones prior to the actual melamine separation through centrifugation, the resulting melamine has an even grain size distribution without larger fine dust portions.

The following examples demonstrate the chemical principles of the process according to the invention by way of example of ethylene glycol as the liquid, organic phase, without hereby limiting the suitability and use of the others afore-mentioned components.

EXAMPLE 1

An ammonia-saturated melamine melt with a starting content of 9500 ppm melam and 500 ppm melem with a temperature of 400° C. and a pressure of 12 MPa was decompressed from one autoclave into a second autoclave, which contained ethylene glycol of 250° C. at a pressure of 7 MPa. After a residence time of 30 minutes under these conditions, the resulting solution of melamine was cooled in ethylene glycol, and the crystallized melamine as well as the mother liquor were analyzed.

In the mother liquor no decomposition products of ethylene glycol could be found.

Likewise the crystallized melamine was free from oxotriazines, the melam content had dropped to below 1000 ppm, the melem content was <100 ppm.

EXAMPLE 2

A melamine-containing gas at 350° C. having the composition of 2% by volume melamine, 6% by volume carbon dioxide and 92% by volume ammonia was introduced into 150° C. hot ethylene glycol at atmospheric pressure. From the resulting melamine/ethylene glycol solution having a melamine content of 6.5% by weight the melamine was crystallized out by cooling it to 50° C. After washing the melamine had a purity level of 99.8%, in the mother liquor no oxotriazines or decomposition products of the ethylene glycol could be found.

The invention claimed is:

1. A process for the continuous cooling and crystallization of solid melamine from the gaseous phase or from melamine melts as they develop in technical processes used to produce melamine, wherein a melamine-containing process gas or an ammonia-saturated melamine melt from a high-pressure process is quenched and/or brought in contact with a liquid, organic phase of ethylene glycol, polypropylene glycol, glycerine or mixtures thereof, wherein the melamine-containing process gas or ammonia-saturated melamine melt cools off without forming decomposition or hydrolysis products, is converted into a solution or suspension of melamine in said liquid, organic phase, from which through further cooling and crystallization, melamine is obtained, and the liquid, organic phase is returned to the process.

2. Process according to claim 1, wherein the cooling or quenching of melamine-containing process gases or a melamine melt occurs at temperatures between 100° C. and 350° C., preferably at temperatures of 100° C. to 300° C.

3. Process according to claim 1, wherein quenching of a melamine melt occurs with a liquid, organic phase at a pressure of 1 to 13.5 MPa, preferably 3 to 8 MPa.

4. Process according to claim 1, wherein the melamine solution or suspension developing in the quencher is decompressed of 0.1–0.5 MPa before separating or further crystallizing the melamine in a separator and that hereby gases still contained therein such as ammonia, carbon dioxide and decomposition products of the unreacted urea are removed from the solution or suspension.

5. Process according to claim 1, wherein the ammonia concentration in the liquid phase of the quencher does not increase to above 40% by weight, preferably is kept below 20% by weight.

6. Process according to claim 1, wherein the melamine, which has been dissolved in the liquid, organic phase, is crystallized out through cooling crystallization, that the developing melamine crystals together with suspended melamine are separated by means of hydrocyclones and centrifuges, the mother liquor is returned to the process and the separated melamine crystals are washed in a separate unit with water.

7. Process according to claim 1, wherein the residence time of the precipitated or dissolved melamine in the quencher depending on the selected temperature and pressure conditions is adjusted such that existing by-products such as melem and melam are converted back to melamine.

* * * * *